(12) United States Patent
Le Cocq et al.

(10) Patent No.: US 7,181,373 B2
(45) Date of Patent: Feb. 20, 2007

(54) SYSTEM AND METHODS FOR NAVIGATING AND VISUALIZING MULTI-DIMENSIONAL BIOLOGICAL DATA

(75) Inventors: Christian A. Le Cocq, Menlo Park, CA (US); Rudolf Grimm, Gauting (DE)

(73) Assignee: Agilent Technologies, Inc., Santa Clara, CA (US)

( * ) Notice: Subject to any disclaimer, the term of this patent is extended or adjusted under 35 U.S.C. 154(b) by 365 days.

(21) Appl. No.: 10/918,598

(22) Filed: Aug. 13, 2004

(65) Prior Publication Data

US 2006/0036425 A1 Feb. 16, 2006

(51) Int. Cl.
*G06F 17/50* (2006.01)

(52) U.S. Cl. .......................................... 703/1; 382/299

(58) Field of Classification Search ................ 703/1; 382/298–300; 358/1.2; 700/98; 348/208.06
See application file for complete search history.

(56) References Cited

U.S. PATENT DOCUMENTS 5,125,043 A * 6/1992 Karlsson ................... 382/300
6,287,765 B1 * 9/2001 Cubicciotti ................... 435/6
6,904,176 B1 * 6/2005 Chui et al. ................. 382/240
7,102,541 B2 * 9/2006 Rosenberg ................... 341/20
7,113,789 B1 * 9/2006 Boehmke .................... 455/446

OTHER PUBLICATIONS

Soga et al., Quantitative Metabolome Analysis Using Capillary Electrophoresis Mass Spectrometry. vol. 2, No. 5, pp. 488-494. Published on Web Jun. 28, 2003.
Liebler, Introduction to Proteomics, Humana Press, Totowa, NJ, pp.v, and Mar. 13, 2002.

* cited by examiner

*Primary Examiner*—Albert W. Paladini

(57) ABSTRACT

Methods systems and computer readable media for manipulating and displaying sparse data contained within very large datasets. Particular applications includes those to proteomics and metabolomics. Navigation of the large data sets from a global perspective may be practically implemented, so that a user is not confined to a narrow slice of data at a time, thus providing context of the whole dataset while viewing data within the dataset.

38 Claims, 12 Drawing Sheets

Fig. 12 — Prior Art

SYSTEM AND METHODS FOR NAVIGATING AND VISUALIZING MULTI-DIMENSIONAL BIOLOGICAL DATA

FIELD OF THE INVENTION

The present invention pertains to the navigation and visualization of large datasets. More particularly, the present invention relates to navigation and visualization of large, multi-dimensional biological or chemical datasets generated by high-throughput experimental procedures.

BACKGROUND OF THE INVENTION

Working with extremely large datasets can be problematic to a researcher in terms of trying to maintain an appropriate amount of detail of the subject data being examined, while at the same time maintaining sufficient context of the surrounding data. This problem is amplified when the data of interest is extremely sparse, spread out over a very large dataset.

In the biological field, these problems present with respect to many different forms of large datasets that researchers need to study. With the advent of high throughput technologies, dataset sizes and the volumes of data available for the researcher to access have grown by magnitudes.

One of the areas in biology in which the data to be studied is particularly sparse within very large datasets, is in the field of proteomics. One method of attempting to identify the proteins that are present in a sample is through protein expression profiling. Protein expression profiling involves the identification of proteins in a particular sample as a function of a particular state of the cell or as a function of exposure to a drug, chemical, or physical stimulus. One common approach to protein expression profiling is through the use of mass spectrometry, wherein proteins are fragmented, such as by digestion of the proteins, and then processed in a mass spectrometer. Another approach to protein expression profiling is the use of protein microarrays.

Another area in biology characterized by sparse data within very large datasets is the field of metabolomics. Metabolomics is the study of cellular metabolites, the small molecules that are the intermediates and products of metabolism. Metabolism refers to the totality of chemical changes that occur within tissues of an organism during the buildup and breakdown of molecules for utilization by the body. As with proteomics, one common approach to metabolomic analysis is through the use of mass spectrometry.

A common workflow for the use of mass spectrometry to, for example, determine the cohort of proteins in a sample of serum, involves the following steps. First, cells are broken down and complex protein mixtures are extracted through a process known as "lysis". "Digestion" is performed to break down proteins in the sample into fragments. The complex mixture of protein fragments is separated into its component fragments. Common laboratory separation techniques include gel electrophoresis and chromatography. It should be noted that in some laboratory techniques the process of separation occurs before digestion. The separated fragments are further prepared and input into a mass spectrometer. A mass spectrometer commonly consists of three functional units. First, a "source" ionizes protein fragments, giving them positive or negative charges. Then, a "mass analyzer" separates the mixture of ions according to their mass-to-charge ratios. A "detector" detects the different ions and drives a data acquisition system that prepares raw mass spectral data. A "mass spectrum" is a plot of data typically containing m/z values along the x-axis and intensity values along the y-axis. The raw mass spectral data is typically interpreted by application software, for example in searching the data against protein databases to provide protein identification.

An example workflow for metabolomic analysis involves separating metabolites in a sample by capillary electrophoresis, then selectively detecting metabolites using mass spectrometry by monitoring over a range of mass/charge values. This is described in Soga et al., "Quantitative Metabolome Analysis Using Capillary Electrophoresis Mass Spectrometry", Journal of Proteome Research, 2003, 2, 488–494.

In addition to working with interpreted data, it is often necessary and desirable for the user to view and interact directly with the raw mass spectral data itself. One example of this is in confirming whether a mass spectrometry experiment has provided coverage across the range of likely peptide fragments expected to be seen in a sample. Directly inspecting the raw mass spectral data is also very useful in estimating the quality of the data. For example, from visual inspection, a user can get a sense of overall signal/noise ratio. From the shape of visual features and from bleeding between visual features, the user can get a sense of the saturation of data in one dimension and the resolution of the data. Additionally, experimental artifacts such as chemical pollution in the source of the mass spectrometer are typically quite visible. Thus, a rough measure of quality is very evident.

Existing software for viewing and interacting with mass spectra is quite complex because there can be hundreds of thousands of compounds involved in the analysis of a typical sample. Current mass spectrometry data visualization software is limited to a narrow cross-section of data at a time, typically a slice of data in one dimension, for example either a sum of intensities over time or distribution of wavelength intensities at one given time point. Thus, while these approaches may provide sufficient detail of the data, they do so while significantly losing context of the surrounding data from which the narrow cross section is taken. This is due to the fact that datasets are enormous and sparse.

Several programs, for example the Analyst QS software product from MDS Sciex (http://www.sciex.com) have the ability to display two-dimensional graphs of mass spectrometry data, for example intensity vs. mass/charge ratio over time, however they for the most part work with fixed images. Changing any aspect of the image boundaries forces a redrawing of the image and/or the creation of a new window. This, in general, is slow and cumbersome.

Because mass spectrometry data is usually sparse and fine-featured, the simple display of scaled down mass spectral data is hard to read. Often the important information in mass spectral data, time and abundance, is visible on only a very small area, typically only a few data points in either direction. These fine features are often grouped together in patches, but these groups of features can often be far apart. Thus, information is lost when the image is zoomed out to a low degree of magnification, as features in the display of the data blend into each other.

The field of cartography deals with similar problems. Although some software systems provide the capability of zooming in and out from detailed views to high level views, these views are not generally continuously zoomable, but must be redrawn at different magnifications, which requires time and the user loses a sense of continuity as well, which can be detrimental to his/her sense of context. See, for example, http://www.mapquest.com/.

Additionally, the state of the art for comparing multiple mass spectrometry data sets is fairly primitive. Although some ad hoc research is being conducted with regard to this problem, the research has tended to be focused on very specific problems. Thus, there is no widely accepted solution to the problem of comparing multiple datasets.

In other domains, there are systems for using a graphical feature as an index for querying a database. An example of this is "content-based image retrieval", as provided in products from Virage, Inc. (http://www.virage.com/), wherein a sample image is provided as input and the system returns a set of images in the database that are most similar, in terms of features such as color, texture or structure, to the sample image. These systems are not adapted to searching large, sparse datasets such as mass spectrometry data.

In view of the existing systems, what is needed are systems, methods, and tools that provide means to easily navigate large, multi-dimensional datasets from a global perspective, instead of being confined to a narrow slice of data at a time, that provide representations of the data at different levels of complexity, and that provide a fast and self-evident interface for zooming in and out so that features of interest are conveniently recognizable.

SUMMARY OF THE INVENTION

The present invention provides methods, systems and computer readable media for displaying and manipulating a large dataset to facilitate identification, correlations or other useful relationships among the data in the dataset. Such displaying and manipulating may be facilitated by generating a planar view of a two-dimensional projection of the data in the dataset; continuously zooming the planar view, to provide a zoomed-in or a zoomed out view of at least a portion of the data, wherein the continuous zooming feature facilitates a user's ability to maintain reference; converting an abstraction of at least a portion of the data to a different level of abstraction during said continuously zooming step when a predetermined level of zooming-in has been reached, and converting the different level of abstraction back to the abstraction of the at least a portion of the data when a predetermined level of zooming-out has been reached.

The planar view may be provided to be continuously scrollable.

A number of representations at the different level of abstraction may be converted to a second different level of abstraction during the continuously zooming step when a second predetermined level of zooming-in has been reached, and, conversely, the second different level of abstraction may be converted back to the different level of abstraction when a second predetermined level of zooming-out has been reached.

Seamless zooming of the view of the entire dataset is provided for varied levels of magnification of the entire dataset.

The conversions may be based on computer data structures including a set of pre-computed compressed bitmaps at various magnifications and a set of pre-computed symbol locations for identifying placement of said symbolic representation.

In addition to those conversions already described, an additional number of conversions to additional levels of abstraction may be performed.

The representations at a different level of abstraction may be symbolic representations which are symbolic of features (data), and representation at the second different level of abstraction may include composite symbolic representations of groups of the symbolic representations at the different level of abstraction.

The conversion of a number of said symbolic representations to a composite symbolic representation at the second different level of abstraction may include merging the symbolic representations at the different level of abstraction into the composite symbolic representation at the second different level of abstraction, wherein the composite symbolic representation represents the symbolic representations.

The continuous zooming may be performed in at least one dimension selected from the group consisting of: horizontal dimension, vertical dimension, and both horizontal and vertical dimensions.

During continuous zooming, the planar view may be updated via sub-sampling of the data provided in a detailed bitmap representation.

Such sub-sampling may include selecting a pixel having the maximum intensity, relative to all other pixels sampled in the sub-sample, and representing the sub-sampled group of pixels with the intensity of the selected pixel.

Further, continuous zooming may include merging a multiplicity of symbolic representations into a composite symbol representative of the multiplicity of symbolic representations.

Large datasets that may be manipulated and displayed by the present invention include mass spectrometry datasets. Such mass spectrometry datasets may include data represented in terms of intensity values per Dalton per time unit.

The present invention is particularly well suited for manipulation and display of large datasets in which the data therein is sparsely distributed in the large dataset.

Methods, systems and computer readable media are provided for comparing multiple, large scale datasets, by fitting equal scales and origins to views of each large scale dataset to be compared, so that a reference to a location on a view of one of the views points to the same corresponding location on all other views; overlaying the views on one display; and visually representing data in each view to visually distinguish from corresponding data in all other views.

The views may be visually distinguished by color-coding the data in the different view with different colors.

Such color-coding may include mapping signal intensity value of data points from the large scale datasets to a scale of intensity values assigned to a range of colors.

Further features of the invention include selecting a feature in the view of the data, and entering at least one annotation that is to be associated with the selected feature of the data.

Various techniques for selection of a feature include lassoing" the feature with mouse movement, mouse clicking, etc.

Annotation entry may be accomplished via an object editor interface, free-form sketching, attachment of an external data file, or the like.

Further, annotations may be overlaid on the view of the data.

Although any large scale datasets may be manipulated and displayed by the present invention, the present invention is particularly well suited to display and manipulation of large scale datasets including sparsely distributed data, including, but not limited to mass spectrometry datasets, such as mass spectrometry datasets including proteomics data or metabolomics data; biological datasets; and chemical datasets.

The present methods systems and computer readable media may provide for selecting a portion of the data in a dataset and automatically querying at least one database, based on the selection made.

The database query may trigger display of retrieved data in an associated viewer software.

Selection of a segment of data in the associated viewer software may trigger scrolling to display a set of features in the dataset that correspond to the segment of data in the associated viewer.

Methods of forwarding a result, transmitting data representing a result, and/or receiving a result obtained from any of the above methods is also covered by the present invention.

These and other advantages and features of the invention will become apparent to those persons skilled in the art upon reading the details of the invention as more fully described below.

DETAILED DESCRIPTION OF THE INVENTION

Figure 1:
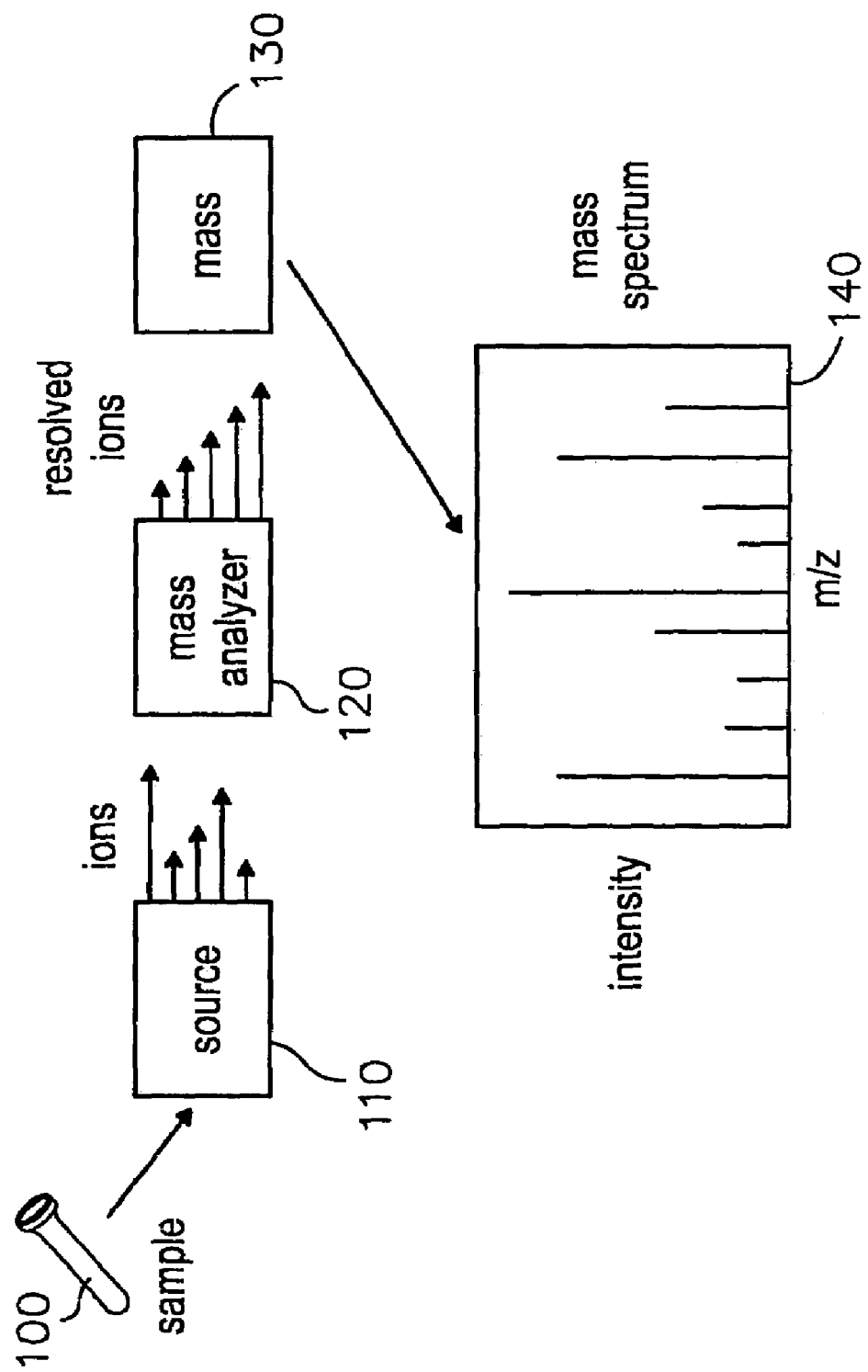
FIG. 1 is a schematic representation of a typical mass spectrometry workflow.

Before the present methods, tools and system are described, it is to be understood that this invention is not limited to particular data sets, manipulations, tools or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a protein" includes a plurality of such proteins and reference to "the mass spectrograph" includes reference to one or more mass spectrograph and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the present application, unless a contrary intention appears, the following terms refer to the indicated characteristics.

The term "proteomics", as described in Liebler, D. "Introduction to Proteomics: Tools for the New Biology, *Humana Press,* 2003, refers to the analysis of large sets of proteins. Proteomics deals with the identification and quantification of proteins, their localization, modifications, interactions, activities, and their biochemical and cellular function. The explosive growth of the proteomics field has been driven by novel, high-throughput laboratory methods and measurement technologies, such as gel electrophoresis and mass spectrometry, as well as by innovative computational tools and methods to process, analyze, and interpret huge amounts of data.

"Mass Spectrometry" (MS) is a technique for measuring and analyzing molecules that involves fragmenting a target molecule, then analyzing the fragments, based on their mass/charge ratios, to produce a mass spectrum that serves as a "molecular fingerprint". Determining the mass/charge ratio of an object is done through means of determining the wavelengths at which electromagnetic energy is absorbed by that object. There are several commonly used methods to determine the mass to charge ration of an ion, some measuring the interaction of the ion trajectory with electromagnetic waves, others measuring the time an ion takes to travel a given distance, or a combination of both. The data from these fragment mass measurements can be searched against databases to obtain definitive identifications of target proteins. In this way the researcher can identify as many as possible of the proteins in a sample. There are many other applications of mass spectrometry. Protein expression profiling involves the identification of proteins in a particular sample as a function of a particular state of the cell or as a function of exposure to a drug, chemical, or physical stimulus. Protein network mapping concerns determining how proteins interact with each other in living systems. Protein modifications mapping involves identifying protein modifications, such as phosphorylation. Mass spectrometry is also widely used in other areas of chemistry, like petrochemistry or pharmaceutical quality control, among many others.

The term "proteomics" refers to analysis of large sets of proteins, more specifically the identification and quantification of proteins, their localization, modifications, interactions, activities, and their biochemical and cellular function.

The term "identification" refers to the determination of the existence of a protein fragment in a sample, or, in general, to the identification of a compound of interest in a sample. One method of identification involves, as mentioned above, searching a database of compounds having been previously identified or linked with their mass spectrometry signatures.

The term "lysis" refers to cell rupture caused by physical or chemical means. This is done to obtain a protein extract from a sample of serum or tissue.

The term "digestion" refers to breaking down a protein into fragments.

The term "separation" refers to separating a complex mixture into its component proteins or metabolites. Common laboratory separation techniques include gel electrophoresis and chromatography.

The term "gel electrophoresis" refers to a technique for separating and purifying molecules according to the relative distance they travel through a gel under the influence of an electric current. Techniques for automated gel spots excision may provide data in large dataset format that may be used as input for the methods and systems described herein.

The term "capillary electrophoresis" refers to an automated analytical technique that separates molecules in a solution by applying voltage across buffer-filled capillaries. Capillary electrophoresis is generally used for separating ions, which move at different speeds when the voltage is applied, depending upon the size and charge of the ions. The solutes (ions) are seen as peaks as they pass through a detector and the area of each peak is proportional to the concentration of ions in the solute, which allows quantitative determinations of the ions.

The term "chromatography" refers to a physical method of separation in which the components to be separated are distributed between two phases, one of which is stationary (stationary phase) while the other (the mobile phase) moves in a definite direction. Chromatographic output data may be used for manipulation by the present invention.

The term "chromatographic time", when used in the context of mass spectrometry data, refers to the elapsed time in a chromatography process since the injection of the sample into the separation device. A "mass analyzer" is a device in a mass spectrometer that separates a mixture of ions by their mass-to-charge ratios.

A "source" is a device in a mass spectrometer that ionizes a sample to be analyzed.

A "detector" is a device in a mass spectrometer that detects ions.

An "ion" is a charged object formed by adding electrons to or removing electrons from an atom.

A "mass spectrum" is a plot of data produced by a mass spectrometer, typically containing m/z values on x-axis and intensity values on y-axis.

A "peak" is a point on a mass spectrum with a relatively high y-value.

The term "m/z" refers to the dimensionless quantity formed by dividing the mass number of an ion by its charge number. It has long been called the "mass-to-charge" ratio.

The term "semantic zoom" refers to a visualization technique in which an object's appearance and representation changes as the user zooms closer to or further away from the visualization.

A "Dalton" is a unit of mass equivalent to one-twelfth the mass of a carbon 12 atom in its ground state. 1 Dalton=$1.6605402\times10^{-27}$ kilograms A "heat map" is a data presentation technique for tabular data in which data values are mapped to a continuous range of color values (the relative "heat" of the data value) and the resulting color matrix displayed as a visual map.

An "amino acid" is an organic compound that generally contains an amino (—NH2) and a carboxyl (—COOH) group. Twenty alpha-amino acids are the sub-units that are polymerized to form proteins. Typically a peptide consists of less than 50 amino acids while a protein has greater than 50 amino acids.

A "peptide" is an organic compound that is composed of amino acids.

A "polypeptide" is a peptide containing ten or more amino acids.

A "protein" is a naturally occurring and synthetic polypeptide having a molecular weight greater than about 10,000.

The term "metabolism" refers to the chemical changes that occur within the tissues of an organism, including "anabolism" and "catabolism". Anabolism refers to biosynthesis or the buildup of molecules and catabolism refers to the breakdown of molecules.

A "metabolite" is an intermediate or product resulting from metabolism. Metabolites are often referred to as "small molecules".

The term "metabolomics" refers to the study of cellular metabolites.

A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another.

The term "annotation" is used herein to refer to an explanatory or critical note that may be associated with any item, collection, story element, diagram node, or diagram interaction. Data items may be annotated with respect to visualization of any datasets.

The term "feature" refers to a grouping of data points that are of interest to an experimenter. In mass spectrometry data, a feature can typically consist of a group of peaks.

A "database" refers to a collection of data arranged for ease and speed of search and retrieval. This term refers to an electronic database system (such as an Oracle™ database) that would typically be described in computer science literature. Further this term refers to other sources of knowledge including textual documents, diagrams, experimental results, handwritten notes or drawings, or a collection of these.

When one item is indicated as being "remote" from another, this is referenced that the two items are at least in different labs, offices or buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

"May" means optionally.

Methods recited herein may be carried out in any order of the recited events which is logically possible, as well as the recited order of events.

All patents, patent applications and other references cited in this application, are incorporated into this application by reference except insofar as they may conflict with those of the present application (in which case the present application prevails).

Reference to a singular item, includes the possibility that there are plural of the same items present.

The present invention provides a novel way to navigate and visualize large datasets and is particularly useful when such large datasets contain only sparsely distributed data points and/or features. Though the invention is described with reference to specific examples for use with multidimensional mass spectrometry data, it is not limited to such uses, but rather applies to any problem domain characterized by large, multi-dimensional datasets that can be viewed from different levels of abstraction.

FIG. 1 shows a schematic of a typical mass spectrometry system. A sample 100 is introduced into a source chamber 110, which produces ions from the sample. These ions are fed into a mass analyzer 120, which resolves the different ions based upon a ratio of their mass to their charge (m/z). The resolved ions are detected by a detector 130 and data is produced which maps the intensity of signals at different mass/charge ratios over time. Data display 140 shows one time-slice worth of intensity vs. m/z data.

The data are typically recorded by a data acquisition system and can then be input to data interpretation software. For example the data can be searched against databases to obtain definitive identification of target proteins.

Figure 2:
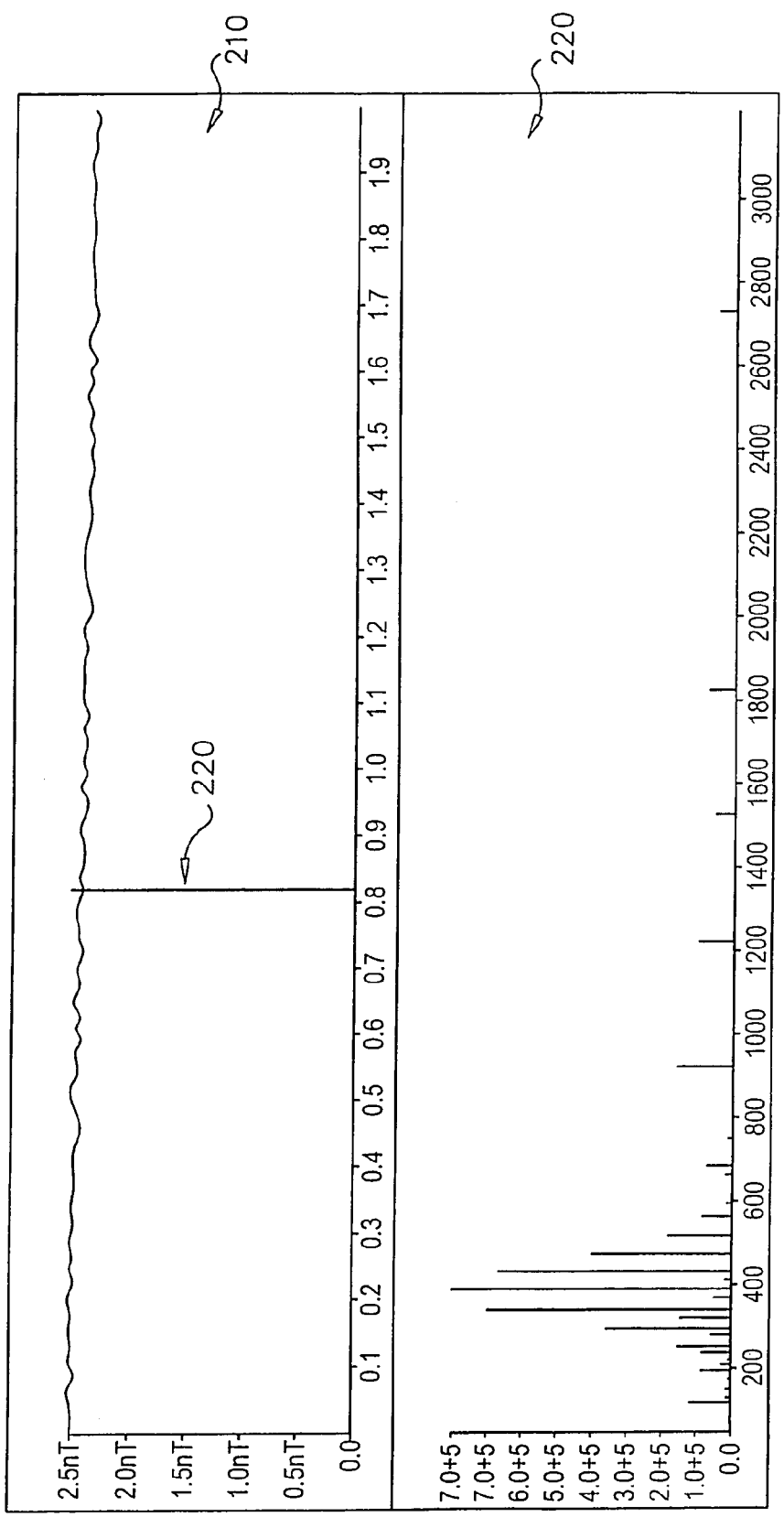
FIG. 2 shows a display from an existing mass spectrometry software product that contains two cross-sectional views of the multi-dimensional data.

In addition to computationally interpreting the data, for example searching the data against protein databases to provide protein identification, it is often necessary for the user to view and interact directly with actual mass spectral data. One example of this is in confirming whether a mass spectrometry experiment has provided coverage across the range of likely peptide fragments expected to be seen in a sample Current software for viewing and interacting with mass spectra is quite complex because there can be hundreds of thousands of compounds involved in the analysis of a typical sample. Current mass spectrometry data visualization software is limited to a narrow cross-section of data at a time, typically a slice of data in one dimension, for example either sum of intensities over time or distribution of wavelength intensities at one given time point. FIG. 2 shows a display 200 from a known mass spectrometry software product that contains two cross-sectional views of the multi-dimensional data. The top-right panel 210 depicts a graph that shows a slice of data along one dimension, in this case the sum of all mass spectral intensities plotted over chromatographic time. The bottom-right panel 220 depicts a graph that shows a slice of data along a different dimension, in this case individual mass spectral intensities plotted against mass/charge ratio at one given time point, which is identified by line 220 in graph 210. Thus, the graph 200 is effectively the result of taking a slice through the data graphed in graph 210 in a direction into the page, rotating it by ninety degrees and displaying in the two-dimensional format shown in graph 220.

Presently known software for interacting with mass spectra work, for the most part, with fixed images. Changing any aspect of the image boundaries forces a redrawing of the image and/or the creation of a new window. This, in general, is slow and cumbersome.

Because the data is sparse and fine-featured, the simple display of scaled down mass spectral data is difficult, if not impossible to read. Often the important information in mass spectral data, such as time, and abundance is visible on only a very small area, typically only a few data points in either direction. These fine features are often grouped together in patches, but these groups of features can often be far apart. Thus, information is lost when the image is zoomed out to a low degree of magnification, as features in the display of the data blend into each other.

Figure 3:
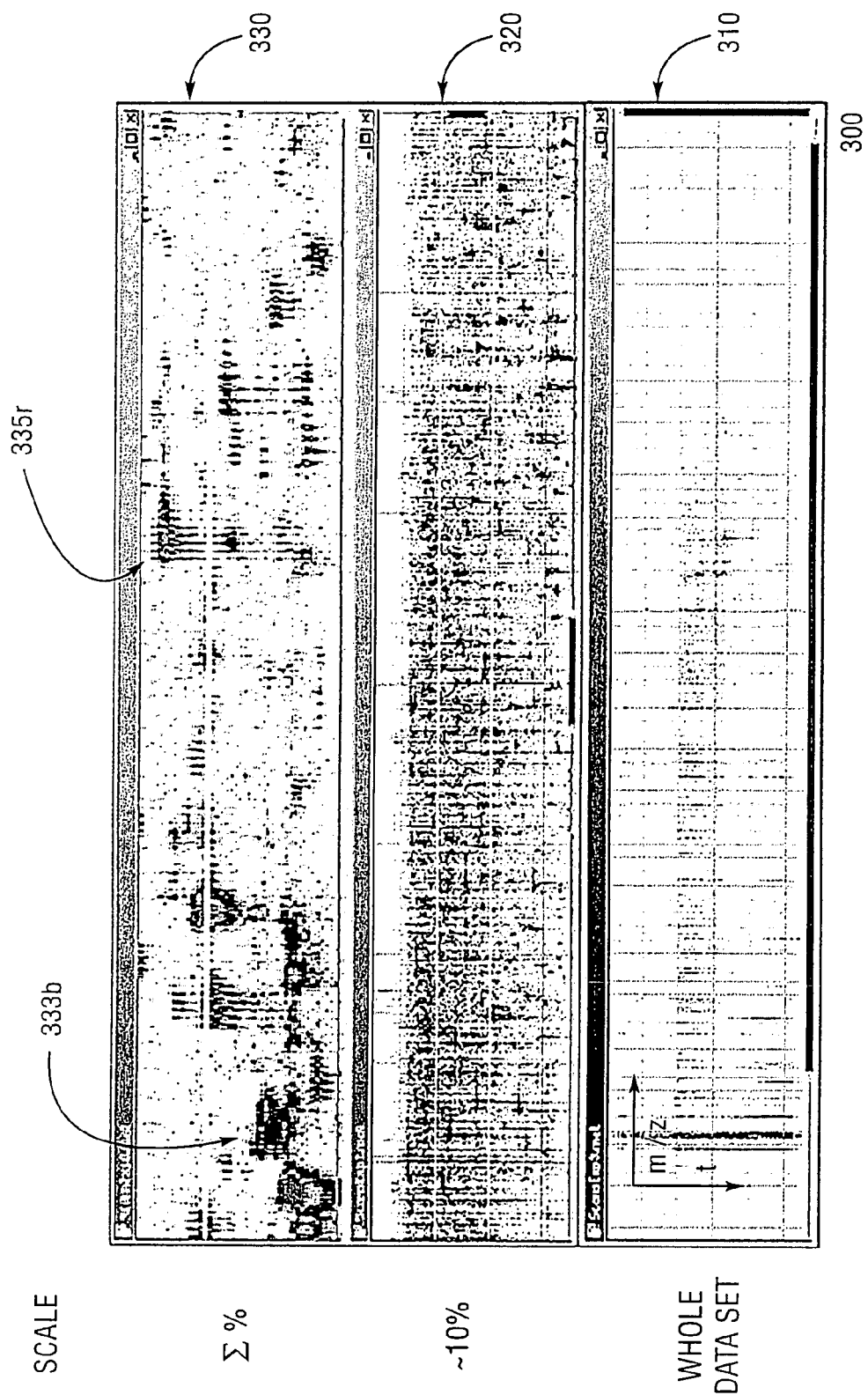
FIG. 3 shows a set of two-dimensional views of multi-dimensional mass spectrometry data, seen from three levels of magnification.

FIG. 3 shows a set of two-dimensional views of mass spectrometry data 300, seen from three levels of magnification. The three panels 310, 320, and 330 are plots of mass data across time (vertical axis), mass/charge ratio (horizontal axis), and intensity (color range from blue 333$b$ to red 335$r$. The lowermost panel 310 contains a display of the entire dataset. Not much information is discernable in this panel. The middle panel 320 contains a 10× magnification of the display in lower panel 310, and thus shows 10% of the dataset. Again, not many features are discernable here. The topmost panel 330 displays a user-selected small subset of "ε%" of the data. In typical mathematical convention, the term "ε" signifies a "very small" quantity. As can be seen, only the topmost panel 330 displays any easily discernable features.

The present system displays a planar view of a 2-dimensional projection of the data, that is typically presented as a "heat map", in which data values are mapped onto a continuous color range, e.g. from blue to red to display the third dimension, which is an intensity scale. Alternative formats for presentation that may be used include contour lines or three-dimensional, drafting style perspective views (e.g., see MATLAB, http://www.mathworks.com/). However, contour lines are expensive to compute and don't scale as well as compared to using the heat map style of presentation, and front row features of three-dimensional perspective views tend to hide or obscure next row features. In any case, the planar representation is continuously zoomable and scrollable, making it natural for the user to switch from global view to detail view, or from one detail location view to global view to another detail location view, or to pan from one detail view to another for example. Data may be mapped to a set of pixel values, with each logical pixel, for example, representing an intensity value at 1 second of chromatographic time (vertical axis), $\frac{1}{10}$ Dalton, and +1 charge. Of course, the pixel scaling may be varied, depending upon the problem at hand and the density of the data. The example given above applies to LC/MS (liquid chromatography/mass spectrometry). GC/MS (gas chromatography/mass spectrometry) for example, would require many more scans than one per second. Typically, for three to five points over a chromatographic peak, this would require about ten scans per second when using GC/MS. Intensity may be mapped into a color value.

Figure 10:
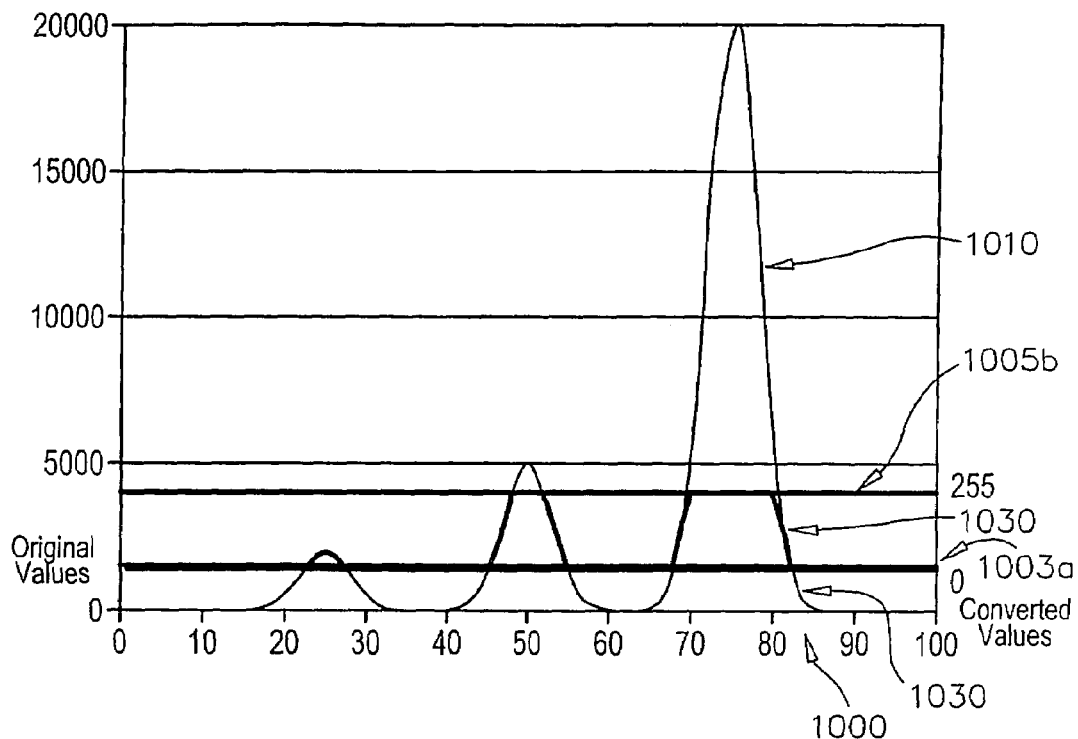
FIG. 10 illustrates an exemplary process of pre-computing a bitmap to represent the raw data.

Reducing the data to the appropriate mix of bitmap and symbols for a given scale can be CPU intensive. In order to make the pan and zoom very fluid and seamless, it is imperative to move as much computation out of the rendition and display phase as possible. Conversely of course, advance computing of display features for all possible display sizes and locations in the data requires large amount of memory to store tables of intermediate results over all the data as well as significant computing time upfront. There are several data preparation regimes for balancing these tradeoffs. One efficient scheme that balances these tradeoffs is shown in FIG. 10. During file input, the abundance and location data is converted into a matrix of n-bit values. The value for 'n' can depend upon the tradeoff desired between expressiveness and efficiency. One efficient tradeoff is to use 1-byte values (ranging from 0–255). The input values are scaled such that "noise" 1030 below a given value 1003a is converted to 0, "high values" 1010 above a value 1005b threshold are mapped to a value 255, and the values in between 1030a and 1005b are linearly mapped to 0–255. This is meant to capture well the transition between baseline and mass spectra peak tops.

To account for the great variety of possible data ranges, the 1003a and 1005b values can be derived from the histogram of data values for each data file, or at least for each family of experiments. Alternatively, the 1003a and 1005b values can be hard coded for each type of data file (i.e. one set for Time-Of-Flight mass spectrometry files, another for Ion Trap mass spectrometry files, etc.). For example, the color range may be expressed by a 16-bit value, resulting in a range from zero for 1003a to 65,336 for 1005b.

Depending on the source file information and the memory available to the program, the size of the matrix, i.e. the density of the abundance information may be scaled as well. One example regime is as follows. The program attempts to create a 1 spectrum per second, 25 points per Dalton matrix. If the data file has fewer than 25 points per Dalton, or if memory cannot accommodate too a large file, the matrix size is reduced proportionally. The data is never extended by interpolation. This is indeed the case for the beginning of a TOF (time of flight) spectrum (resolution changes with mass), where the fragments represented are small, and thus the number of Daltons in the denominator is low. In such cases, the data may be reduced to twenty-five points per Dalton, for example, by integration, i.e., addition with interpolation.

The system employs a principle of constant information density, by providing means for automatically encoding raw data as symbols so that the view switches from raw data to more and more symbolic and simplified representations as the scale gradually goes from detail to global. The visual effects provided by displaying constant information density provide a user with powerful "semantic zooming", characterized by changing of the appearances and representation of objects displayed-as the user zooms closer to or further away from the visualization.

Figure 4:
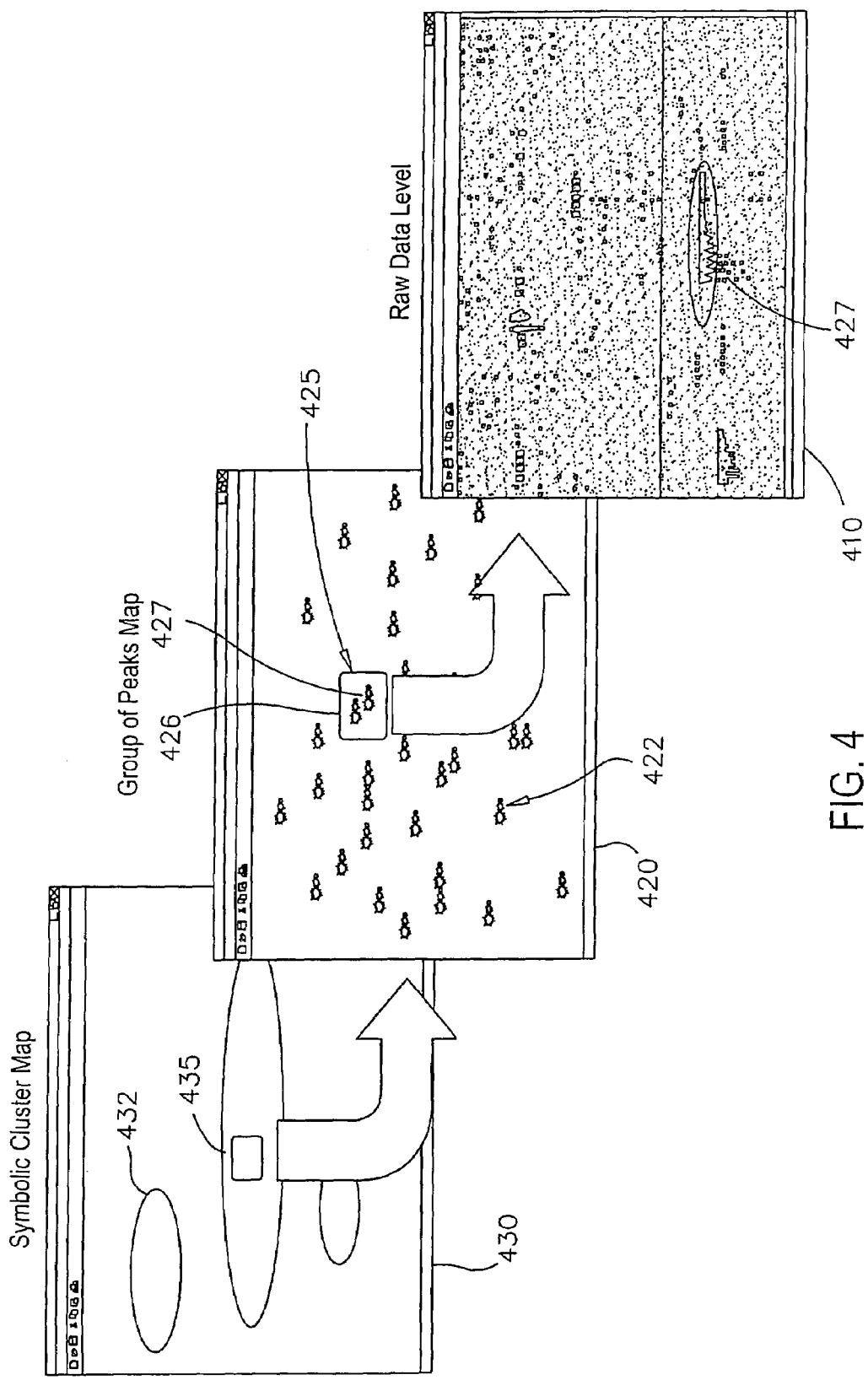
FIG. 4 is a schematic 2D-view of multi-dimensional mass spectrometry data at multiple levels of abstraction.

FIG. 4 is a schematic view of a two-dimensional projection of mass spectrometry data at multiple levels of abstraction. Each level of abstraction represents a viewport into a subset of the total dataset. At the lowest level of abstraction 410, a "raw data level", each pixel in the display corresponds to the smallest amount of information that had been retained during preliminary computation (e.g., $\frac{1}{25}^{th}$ of a Dalton, one second separation time, 255 levels of intensity). At the next higher level of abstraction 420, a "group of peaks map", peaks in the mass spectra that occur close together in the mass/charge and time axes are identified as "features" and each feature is mapped to one graphical symbol 422. Inset box 425 in "group of peaks map" display 420 corresponds to the entire visible display at "raw data level" of abstraction 410. For example, feature 427 at level 420 maps to feature 427 at level 410. The next higher level of abstraction 430 is a "symbolic cluster map". At this level, groups of features are mapped into global symbols 432, for example. All of the features displayed at the group of peaks map level 420 map into the portion of data in the symbolic cluster map that is contained in the inset box 435. The present invention is capable of displaying an arbitrary number of levels of abstraction, for example two levels, or more than three levels, may be employed. The detailed description with respect to three levels. The detailed description of Figure three with respect to three levels, two symbolic and one detailed, has been provided only as an example of the concept of providing the data in different levels of abstraction to facilitate constant information density display, thereby providing the user with semantic zooming.

Figure 5:
FIG. 5 shows mass spectrometry data at a detailed bitmap level of abstraction.

FIG. 5 shows mass spectrometry data at a detailed level of abstraction, showing a full bitmap level of magnification 500.

Figure 6:
FIG. 6 shows mass spectrometry data at a sub-sample bitmap level of abstraction.

FIG. 6 shows mass spectrometry data at a detailed level of abstraction 600, where sub-sampling has been employed to show data at a zoomed-out level of magnification. At this level of magnification, it is possible to see certain features in the data, e.g., 610, 620,630.

Figure 6A:
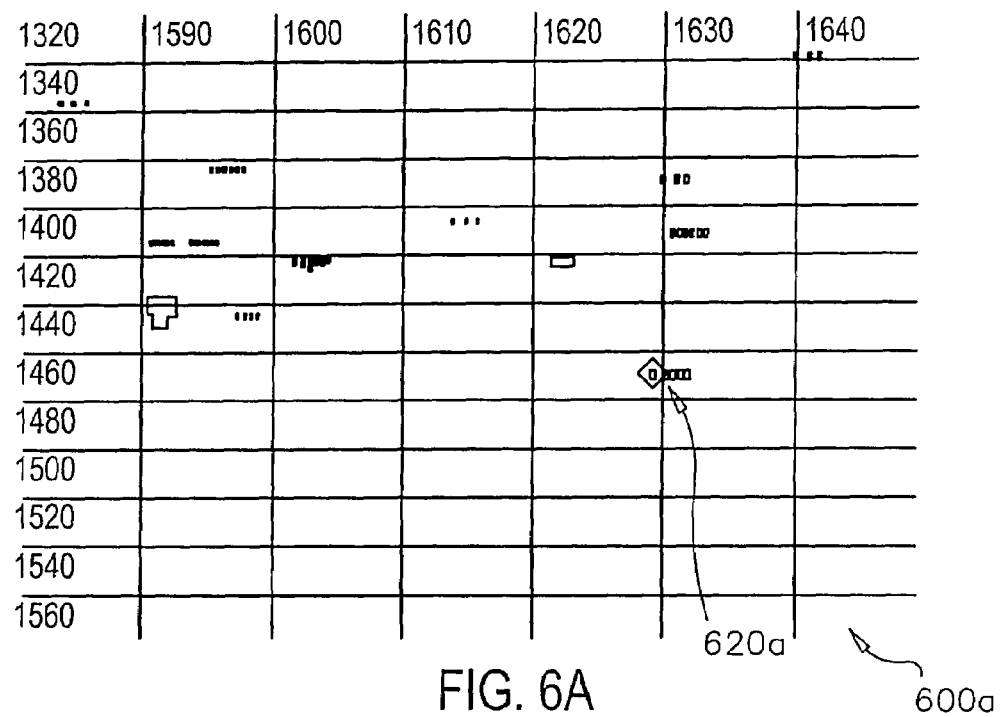
FIG. 6a illustrates a transition between bitmap and symbolic levels of abstraction.

FIG. 6a depicts a transition from detailed to symbolic level of abstraction 600a. As the user zooms out, features shown in 620 in FIG. 6 are mapped to and replaced by a symbolic representation 620a.

Figure 7:
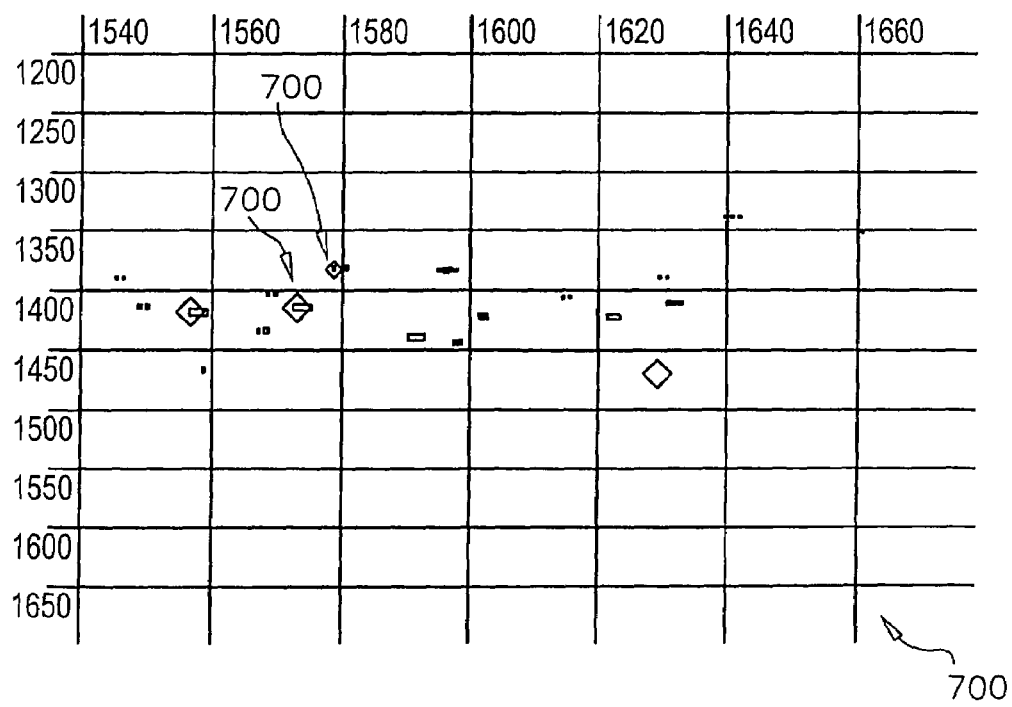
FIG. 7 shows mass spectrometry data at a symbolic level of abstraction, depicting one symbol per feature.

FIG. 7 shows mass spectrometry data at a symbolic level of abstraction 700 that depicts one symbol per feature. Two such symbols are identified in FIG. 7 as 710 and 720.

Figure 8:
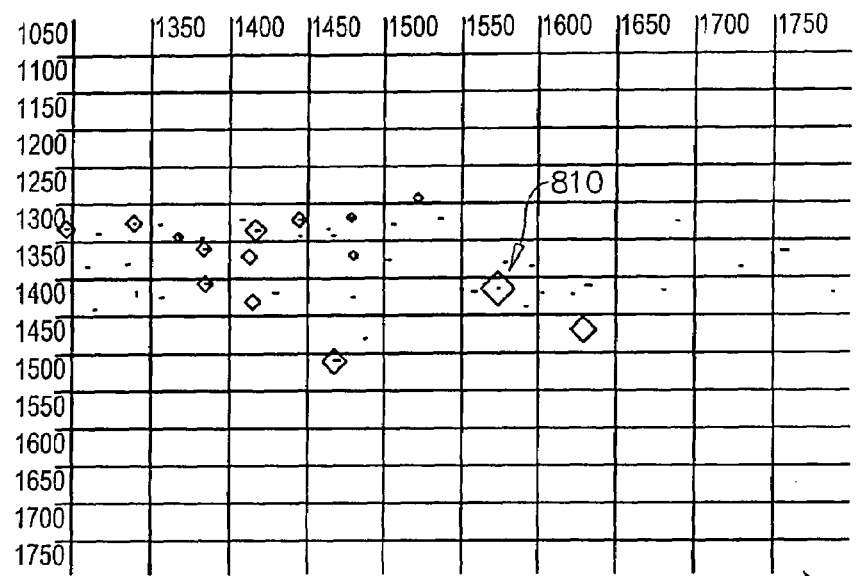
FIG. 8 shows mass spectrometry data at a different magnification of the symbolic level of abstraction shown in FIG. 7.
Figure 8A:
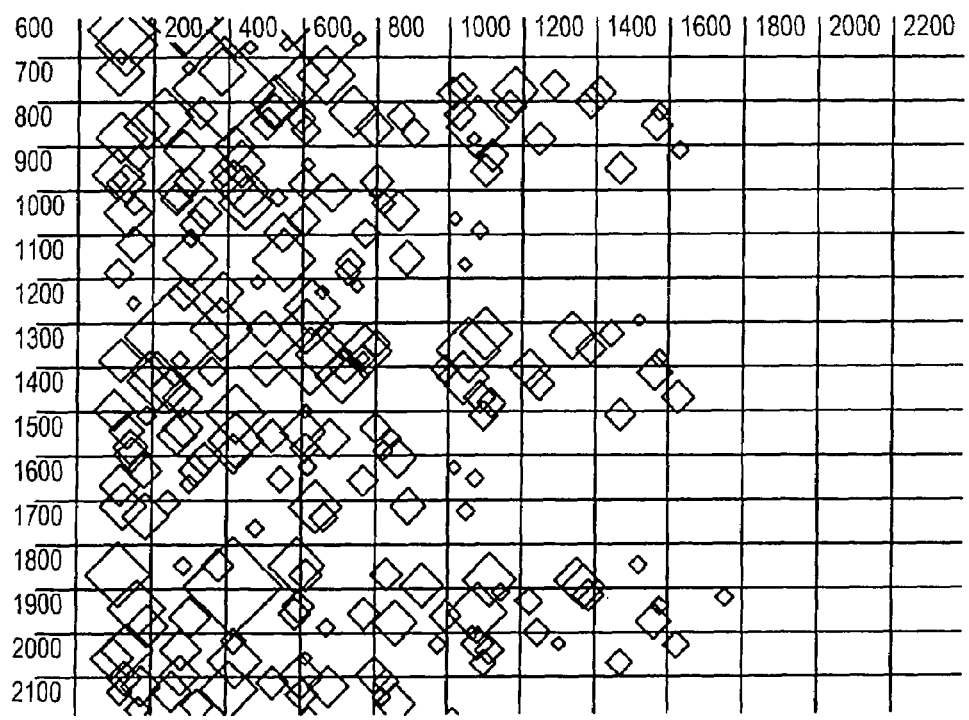
FIG. 8a shows a fully zoomed-out image of mass spectrometry data, depicting one global symbol per group of features.

FIG. 8 shows mass spectrometry data at a symbolic level of abstraction 800, where symbols have been merged upon zooming, resulting in one global symbol per group of features. In this example, symbol 810 is equivalent to the consolidation of symbols 710 and 720.

Figure 9:
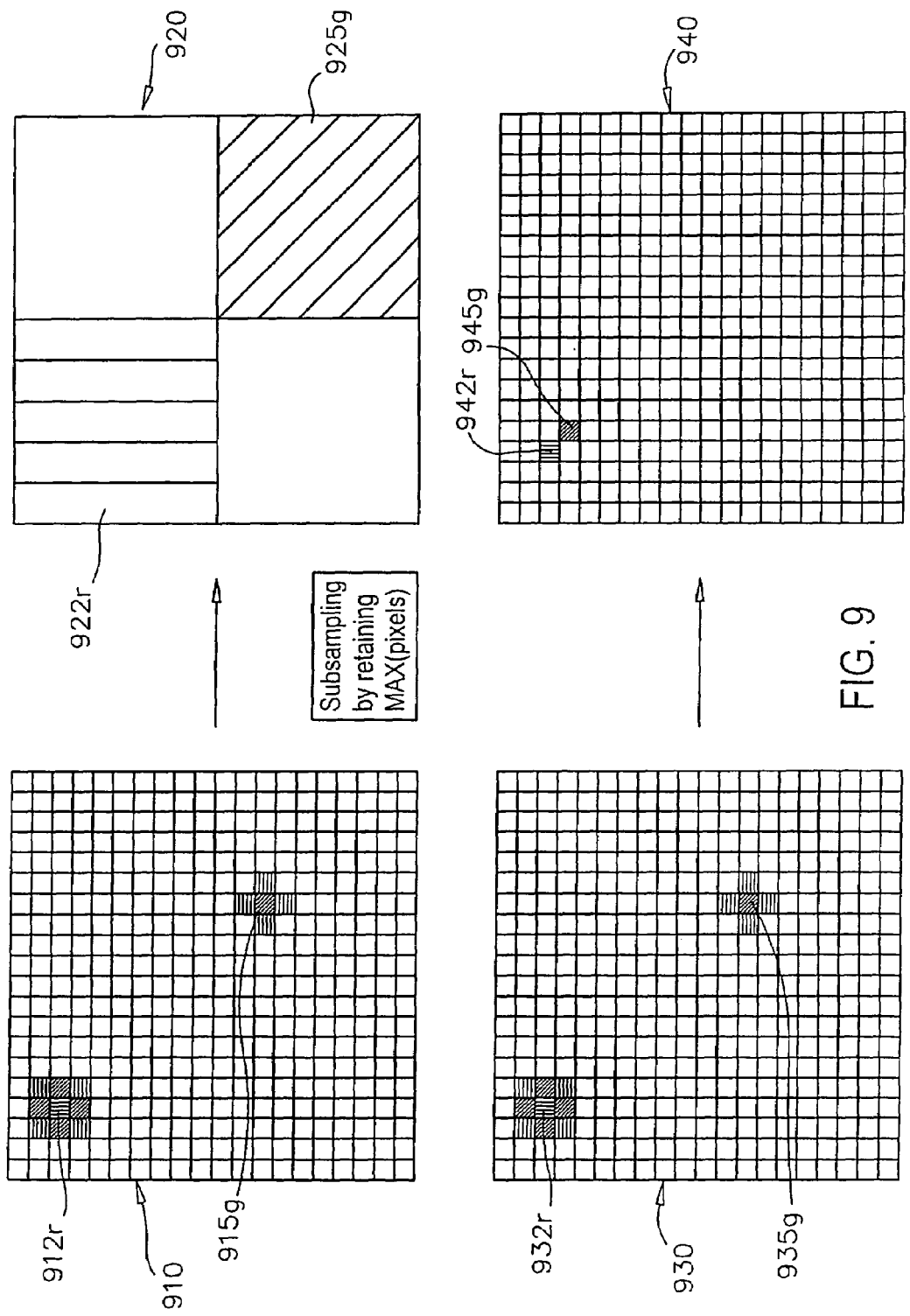
FIG. 9 contains a schematic view of an underlying data organization and sub-sampling mechanism.

While in the detailed level of abstraction, the operations of zooming in or out by the user result in the system updating the display via a sub-sampling mechanism. FIG. 9 is a schematic representation of the sub-sampling mechanism used by the current invention. There are many plausible mechanisms that can be used for sub-sampling, such as pixel averaging or random selection, for example. As an example, a strategy of selecting the maximum intensity pixel of the sample may be used as the representative pixel for the sub-sample. This is done for both zoomed in representation 920 and zoomed out representation 940.

When the user zooms out or in beyond a pre-defined threshold scale factor for a given segment of the display, that segment of display maps to a different level of abstraction. Scale factor can be assessed across any of the displayed dimensions, for example the mass/charge axis. Scale factor of the full density bitmap level of abstraction can be set as a parameter, for example it can be set to 25 points/Dalton. Likewise, the scale factor of the sub-sampled level of abstraction can be set as a parameter, for example it can be set to 1 point/Dalton. When the user zooms out to a scale factor that crosses a pre-defined threshold, for example 2 points/Dalton, the display switches from full density level of abstraction to sub-sampled level of abstraction. When the user zooms out to a scale factor that crosses a second pre-defined threshold, for example 1 point/Dalton, the display switches from sub-sampled level of abstraction to the level of abstraction that depicts one symbol per feature. Conversely, if the user zooms in so that the either of the thresholds are crossed from the opposite direction, for example crossing a threshold of 2 points/Dalton, then the display switches to the appropriate lower level of abstraction, for example switching from sub-sampled level of abstraction to full density level of abstraction.

Zooming can be applied either along each individual axis or globally across both axes. Additionally, the image can be panned vertically or horizontally.

The features described above provide the user with a fast and self-evident user interface, facilitated by rapid and smooth panning and zooming. To achieve a sufficient level of performance when panning and/or zooming over large display data sets, some optimizing techniques are needed. There are several techniques that can be employed. For example, a set of pre-computed compressed bitmaps at various magnifications, may be utilized, the bitmaps generated in the manner described earlier. Additionally, a set of pre-computed symbol locations can be constructed and utilized as follows.

As the aforementioned matrix of data bitmaps is being built, a separate, parallel, and slightly less coarse array is built to allow for the computation of feature centers. The size for each entry of the array is a tradeoff between precision and efficiency. For example, a precision of 16 bits/point can represent up to $2^{16}$ feature centers, whereas a precision of 8 bits/point can represent only up to $2^8$ (or 256) feature centers. To compensate for the added size requirement of 16 bits/entry precision, the feature location computation may be run over subparts of the data and the partial 16-bits/point array is reused as needed.

There are several possible mechanisms for computing the feature centers. The most precise way to compute the feature centers would be to search for all local maximum intensity values and run a 2-D center-of-mass calculation over an area around each maximum. This approach, however, is computationally intensive.

An alternative approach is to utilize a region-labeling algorithm to find all connected regions above a given threshold followed by the computation of the center of all those regions. This can be achieved as follows. For each row in bitmap matrix, examine the intensity value in each column (i.e. examine the intensity value in each cell of the matrix). If the intensity value exceeds a certain threshold, then set the value of the equivalent row and column in the feature centers matrix to a "label", as follows. Look at the immediately adjacent cells for the current cell. If any of those cells has a label, then use the same label. If no adjacent cells have a label, then generate a new label (which indicates the start of a new region). Labels are generated as integer values, starting with 1 for the first label and incrementing for each subsequent label (i.e. 1, then 2, then 3, etc.). After all the labeling is completed, compute the center for each identified region, as follows. A region is characterized by the set of cells in the feature center matrix that have the same label. For each region, the center is defined as the point X, Y where X is the average of all row values for cells in the region and X is the average of all column values for cells in the region. Finally, the array of feature centers is then sorted by X and Y coordinates.

Figure 11:
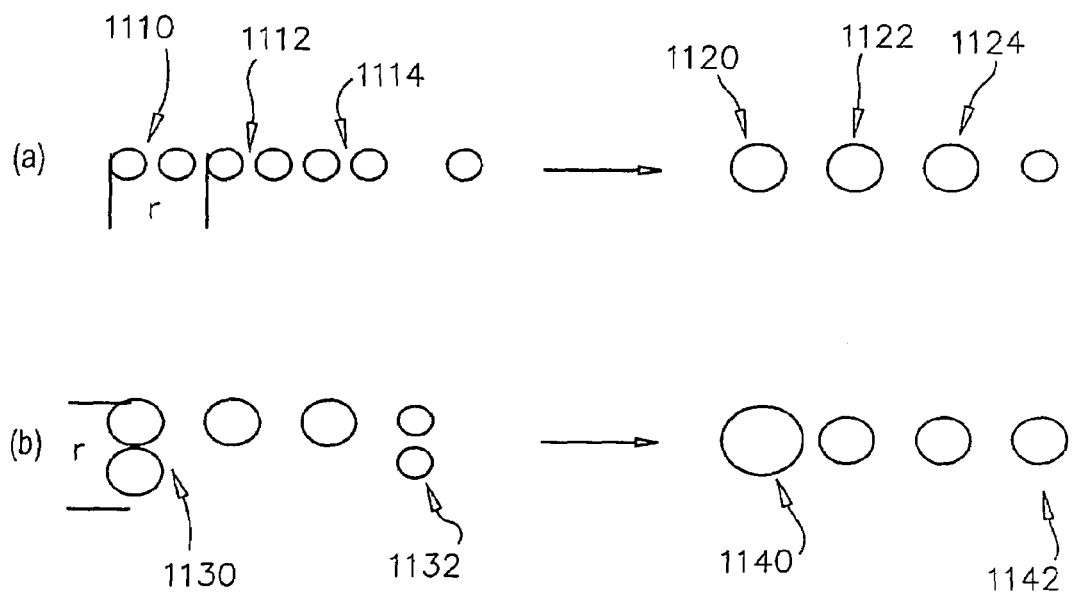
FIG. 11 illustrates an exemplary process of pre-computing positions of symbols to represent potential features.

At display time, the sorted values are converted to screen coordinates and the array is clipped to the viewable area. As some centers can overlap or nearly overlap at screen resolution, one needs to apply some method to disambiguate the resulting picture. There are many methods for accomplishing this. One method is to merge symbols that are deemed to close to each other on screen. This is illustrated in FIG. 11. First, the overlapping symbols are merged onto the lower mass symbol one by one starting by low masses. This is depicted in FIG. 11(*a*), which shows the pairs of symbols 1110, 1112, and 1114 being merged into symbols 1120, 1122, and 1124, respectively. The merging onto lower mass symbol is to accommodate the fact that in mass spectrometry, the chemically meaningful information is often the lowest mass of a cluster of peaks (i.e. an isotopically pure compound mass followed by "modified" compound masses). This merging of symbols thins out a list of consecutive symbols in a comb effect. Next, the remaining symbols are merged again using the same principle, this time along the time axis, also merging into lower time values for reasons similar to those for merging along mass axis. This is depicted in FIG. 11(*b*), where pairs of symbols 1130 and 1132 are merged into symbols 1140 and 1142, respectively.

The present invention provides for comparing multiple datasets by allowing the scale and origin of one dataset view to be fitted onto the view of all the other data sets so that the windows on all the data sets point to homologous locations. Means are provided for overlaying the dataset views with an appropriate choice of colors so as to allow the user to immediately recognize similarities, additions, shifts and size changes in patterns from one data set to the other.

Figure 12:
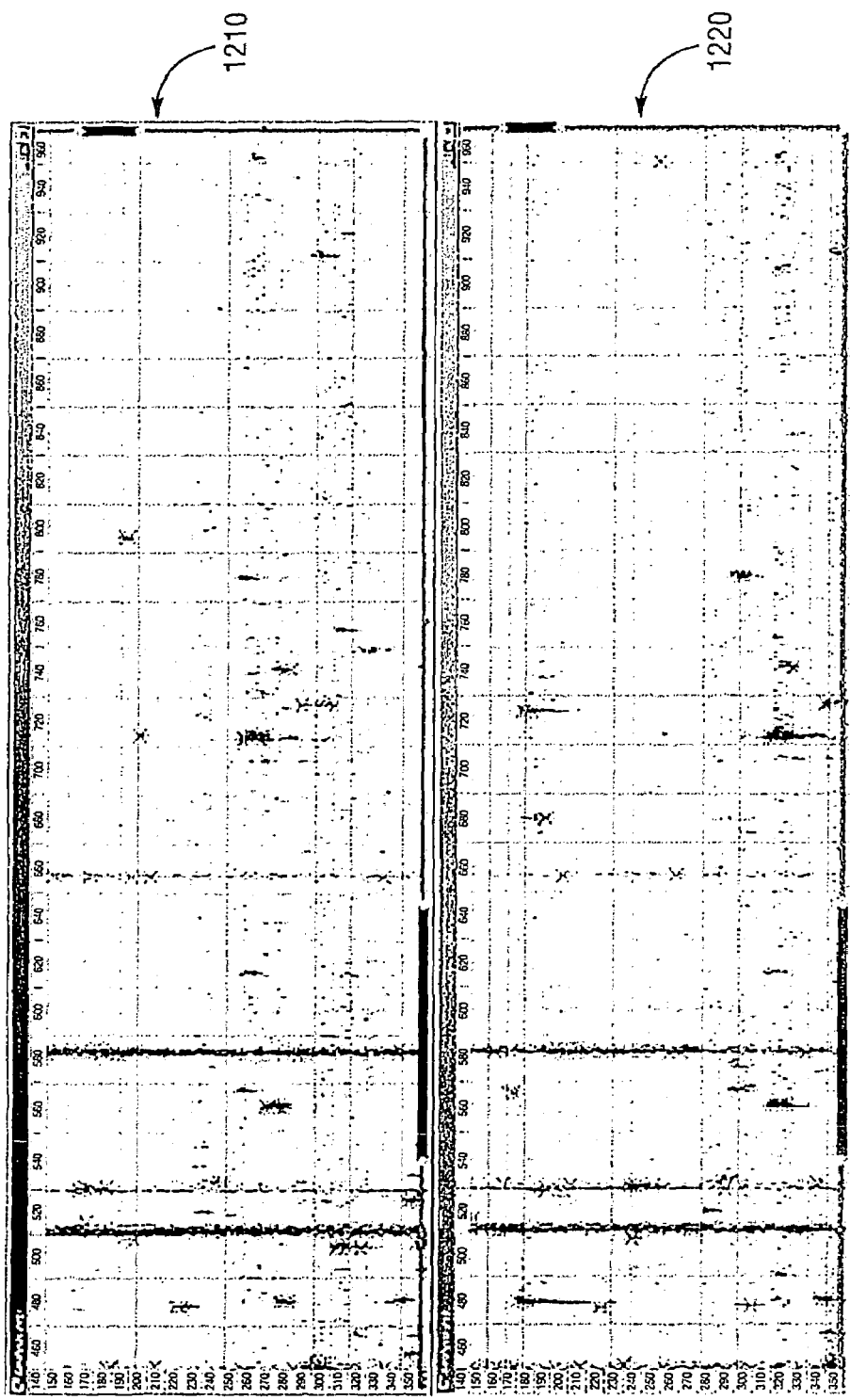
FIG. 12 shows a known approach to comparing mass spectrometry data from multiple datasets.

While comparisons between charts or graphs can currently be accomplished on a viewer, known approaches are fairly limited as to their usefulness. FIG. 12 shows a display that can be achieved using conventional mass spectrometry software products, in which two datasets 1210 and 1220 can be displayed adjacent to each other, with data aligned to the same window origin and scale. It is relatively difficult to visually identify similarities and differences between the two datasets under this approach.

Figure 13:
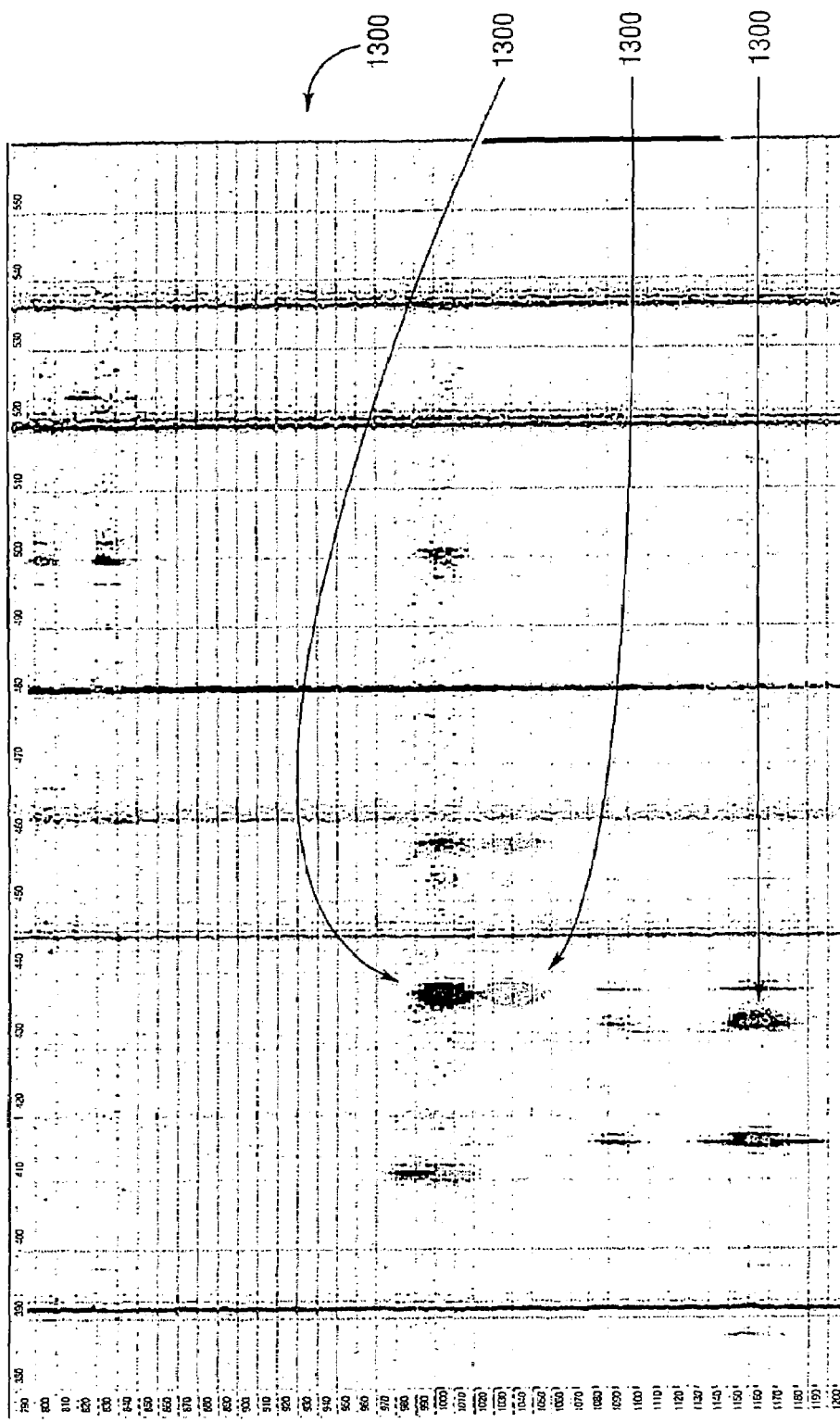
FIG. 13 shows an example of an approach to comparing mass spectrometry data from multiple data sets according to the present invention.

FIG. 13 shows a display achievable using the present invention, in which the data is contained within one window, and overlaid on a single view with different color maps so as to facilitate the immediate recognition of similarities, additions, shifts and size changes in patterns from one dataset to the other. The overlay of color maps is achieved according to principles described in co-pending, commonly assigned application Ser. No. 10/155,405 filed May 22, 2002, and titled "Database Model, Tools and Methods for Organizing Information Across External Information Objects". Application Ser. No. 10/155,405 is hereby incorporated herein, in its entirety, by reference thereto. In the example in FIG. 13, features that appear in only the first dataset are color-coded as blue 1310b, features that appear in only the second dataset are color-coded as green 1320g, and features that appear in both datasets are color-coded as red 1330r.

The current invention provides means for annotating the mass spectrometry data, either manually or computationally. Annotations can easily be overlaid on the mass spectrometry data image, as well as features of the image to be selected as input for further treatment. One method for accomplishing this is to select a feature to annotate via mouse-click operation or by lassoing with mouse-drag operation. This may result in the invocation of an object editor interface for editing and annotating the properties and contents of biological entities, in a manner described in application Ser. No. 10/155,405. Alternatively, the user may add annotation via free-form drawing or attachment of an external data file.

Features of the mass spectrometry data can also be used as inputs to database query operations. The database query could contain mass spectrometry data or any other kinds of data that can be linked to the features. In this way, a mass spectrometry image can serve as a visual "table of contents" for a collection of detailed scientific data, for example a peptide database. If the current invention is operating in a mode wherein it communicates with a viewer software that is capable of displaying the retrieved data, such as the SpectrumMill product from Agilent Technologies, Inc., Palo Alto, Calif, then the selection of a visual feature in the current invention may trigger display of the retrieved data in the associated viewer software. Conversely, selection of a segment of the data in the associated viewer software may trigger the current invention to scroll to display the set of features that correspond to that detailed data. The bi-directional communication between the current invention and the aforementioned data viewer software is achieved in a manner similar to that described in co-pending, commonly owned application Ser. No. 10/641,492 filed Aug. 14, 2003, and titled "Method and System for Data Overlay on a Biological Diagram". application Ser. No. 10/641,492 is hereby incorporated herein, in its entirety, by reference thereto.

Figure 14:
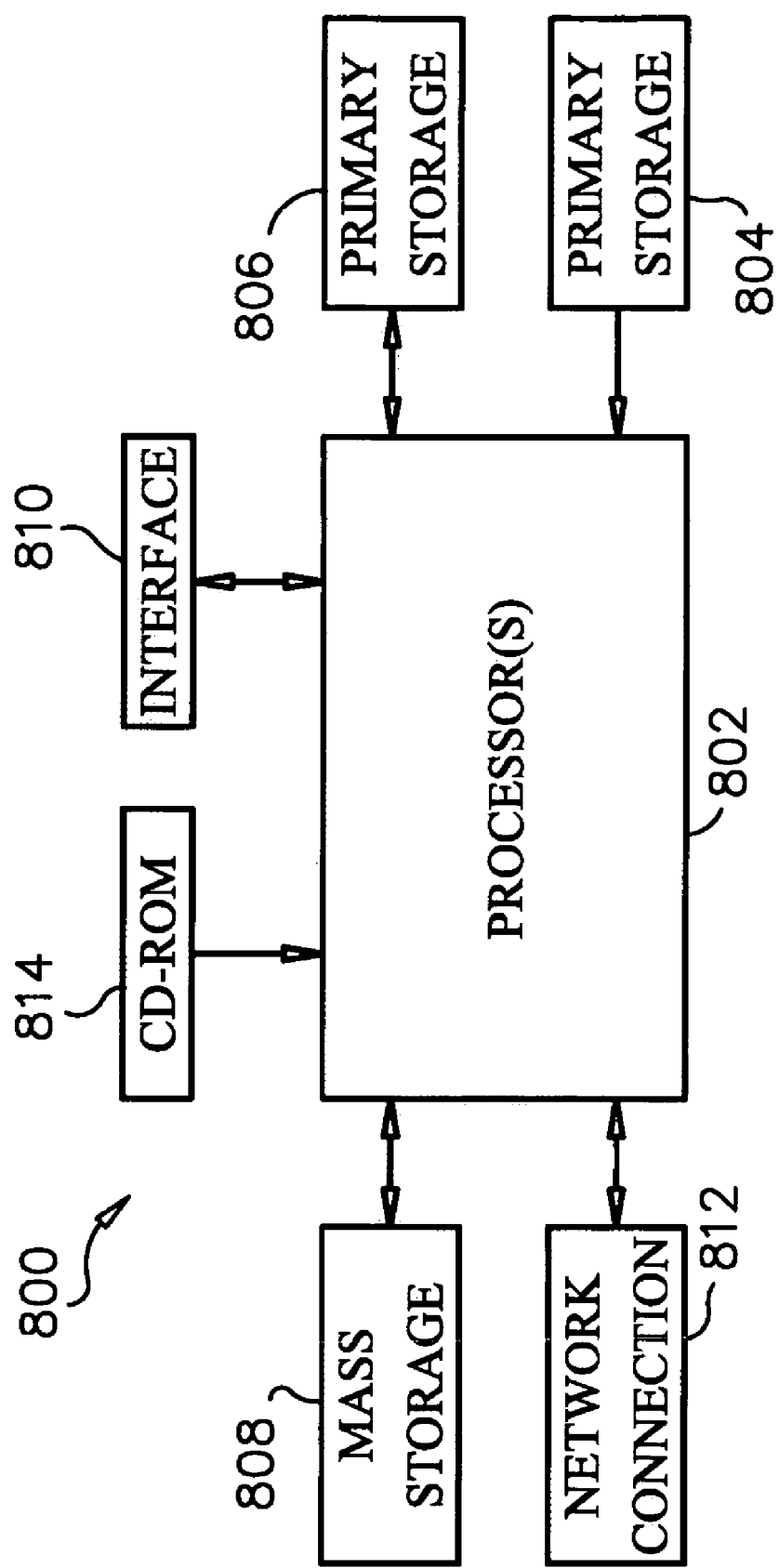
FIG. 14 is a block diagram illustrating an example of a generic computer system which may be used in implementing the present invention.

FIG. 14 illustrates a typical computer system in accordance with an embodiment of the present invention. The computer system 800 includes any number of processors 802 (also referred to as central processing units, or CPUs) that are coupled to storage devices including primary storage 806 (typically a random access memory, or RAM), primary storage 804 (typically a read only memory, or ROM). As is well known in the art, primary storage 804 acts to transfer data and instructions uni-directionally to the CPU and primary storage 806 is used typically to transfer data and instructions in a bi-directional manner Both of these primary storage devices may include any suitable computer-readable media such as those described above. A mass storage device 808 is also coupled bi-directionally to CPU 802 and provides additional data storage capacity and may include any of the computer-readable media described above. Mass storage device 808 may be used to store programs, data and the like and is typically a secondary storage medium such as a hard disk that is slower than primary storage. It will be appreciated that the information retained within the mass storage device 808, may, in appropriate cases, be incorporated in standard fashion as part of primary storage 806 as virtual memory. A specific mass storage device such as a CD-ROM 814 may also pass data uni-directionally to the CPU.

CPU 802 is also coupled to an interface 810 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 802 optionally may be coupled to a computer or telecommunications network using a network connection as shown generally at 812. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for generating a planar view of a two dimensional projection of a dataset may be stored on mass storage device 808 or 814 and executed on CPU 808 in conjunction with primary memory 806.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Systems are provided for displaying and manipulating data to facilitate identification, correlations or other useful relationships among the data. Such systems may include means for generating a planar view of a 2-D projection of the data, which is continuously zoomable and scrollable; and means for reducing raw data to symbols representative of the raw data.

Further the system may be provided with means for reducing symbolic representations to higher levels of composite symbolic representation.

The system may include a set of appropriate computer data structures to allow the whole data set to be visited at any magnification without any apparent seam or transition between zones.

Such data structures may include a set of pre-computed compressed bitmaps at various magnifications as well as a set of pre-computed symbol locations.

Means for reducing symbolic representations to higher levels of composite symbolic representation may be provided to include means for merging multiple symbolic representations into a composite symbolic representation, when a user zooms out while within a symbolic level of abstraction.

Further, means for mapping a segment in the view from a first level of abstraction to a different level of abstraction may be provided and which is responsive to when a user zooms out or in beyond a pre-defined threshold scale factor for the segment.

Means for rapidly zooming with respect to at least one axis of the view may be provided. Such means may zoom with respect to the horizontal axis, the vertical axis, or both the horizontal and vertical axes.

The system may also provide means for rapidly panning the view in a direction selected from the directions consisting of vertical and horizontal.

Means for updating of the view in response to a user zooming the view may be provided, wherein the updating is based on a sub-sampling mechanism.

The raw data manipulated by the system may be mass spectrometry data, for example, represented by intensity values per Dalton per time unit.

Systems for comparing multiple data sets are provided that include means for fitting a scale and origin of one data set view onto views of all other data sets of the multiple data sets, to provide windows on all of the data sets pointing to homologous locations, means for color-coding the fitted data sets to visually distinguish the fitted data sets from each other; and means for overlaying the color-coded, fitted, multiple data set views on a single window.

The data sets may comprise mass spectrometry data.

The color-codings may be produced by mapping signal intensity values of data points in the data sets to a color scale in a blue/red color range.

The system may provide means for triggering a query to at least one external database upon selection of graphical features in the view.

Further, means for displaying results of such a database query in an associated viewer software may be provided.

Means for scrolling in to a set of features in the data upon selection of a segment of the displayed results in the associated viewer software may be provided.

A computer readable medium carrying one or more sequences of instructions for displaying and manipulating data to facilitate identification, correlations or other useful relationships among the data may be provided, wherein execution of one or more sequences of instructions by one or more processors causes the one or more processors to perform the steps of: generating a planar view of a 2-D projection of the data, which is continuously zoomable and scrollable.

Further, the computer readable medium may contain instructions, wherein execution of one or more sequences of the instructions by one or more processors causes the one or more processors to perform the additional step of reducing raw data to symbols to convert the view from raw data to symbolic representations during zooming out on the view.

Further, the computer readable medium may contain instructions, wherein execution of one or more sequences of instructions by one or more processors causes the one or more processors to perform the additional step of generating a set of appropriate computer data structures to allow the data set to be viewed at any available magnification without any apparent seam or transition between views.

Further, the computer readable medium may contain instructions, wherein execution of one or more sequences of instructions by one or more processors causes the one or more processors to perform the additional step of mapping a segment of the view to a different level of abstraction when a user zooms out or in beyond a pre-defined threshold scale factor for said segment.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular model, tool, process, process step or steps, to the objective, spirit and scope of the present invention. All such modifications are intended to be within the scope of the claims appended hereto.

That which is claimed is:

1. A method for displaying and manipulating a large dataset to facilitate identification, correlations or other useful relationships among the data in the dataset, the method comprising the steps of:
   generating a planar view of a two-dimensional projection of the data in the dataset;
   continuously zooming the planar view, to provide a zoomed-in or a zoomed out view of at least a portion of the data, wherein the continuous zooming feature facilitates a user's ability to maintain reference; and
   converting an abstraction of at least a portion of the data to a different level of abstraction during said continuously zooming step when a predetermined level of zooming-in has been reached, and converting the different level of abstraction back to the abstraction of the at least a portion of the data when a predetermined level of zooming-out has been reached.

2. The method of claim 1, wherein said planar view is continuously scrollable.

3. The method of claim 1, further comprising converting a number of representations at said different level of abstraction to a second different level of abstraction during said continuously zooming step when a second predetermined level of zooming-in has been reached, and converting the second different level of abstraction back to the different level of abstraction when a second predetermined level of zooming-out has been reached.

4. The method of claim 1, further comprising seamlessly zooming the view of the entire dataset to provide varied levels of magnification of the entire dataset.

5. The method of claim 1, wherein said converting is based on computer data structures including a set of pre-computed compressed bitmaps at various magnifications and a set of pre-computed symbol locations for identifying placement of said symbolic representation.

6. The method of claim 3, further comprising performance of a predefined additional number of conversions to additional levels of abstraction.

7. The method of claim 3, wherein said representations at said different level of abstraction are symbolic representations which are symbolic of features and wherein said representation at said second different level of abstraction comprise composite symbolic representations of groups of said symbolic representations at the different level of abstraction.

8. The method of claim 7, wherein said converting a number of said symbolic representations to a composite symbolic representation at said second different level of abstraction comprises merging said symbolic representations at the different level of abstraction into said composite symbolic representation at the second different level of abstraction, wherein said composite symbolic representation represents said symbolic representations.

9. The method of claim 1, wherein the step of continuously zooming is performed in at least one dimension selected from the group consisting of: horizontal dimension, vertical dimension, and both horizontal and vertical dimensions.

10. The method of claim 1, wherein said continuously zooming comprises updating the planar view via sub-sampling of the data provided in a detailed bitmap representation.

11. The method of claim 10, wherein said sub-sampling comprises selecting a pixel having the maximum intensity, relative to all other pixels sampled in the sub-sample, and representing the sub-sampled group of pixels with the intensity of the selected pixel.

12. The method of claim 1, wherein said continuous zooming comprises merging a multiplicity of symbolic representations into a composite symbol representative of the multiplicity of symbolic representations.

13. The method of claim 1, wherein the large dataset comprises mass spectrometry data.

14. The method of claim 13, wherein said mass spectrometry data is represented by intensity values per Dalton per time unit.

15. The method of claim 1, wherein the data is sparsely distributed in the large dataset.

16. A method for comparing multiple, large scale datasets, comprising the steps of
fitting equal scales and origins to views of each large scale dataset to be compared, so that a reference to a location on a view of one of the views points to the same corresponding location on all other views;
overlaying said views on one display; and
visually representing data in each said view to visually distinguish from corresponding data in all other views.

17. The method of claim 16, wherein said visually representing comprises color-coding.

18. The method of claim 16, wherein said large scale datasets comprise mass spectrometry data.

19. The method of claim 17, wherein said color-coding comprises mapping a signal intensity value of a data point from one of said large scale datasets to a scale of intensity values assigned to a range of colors.

20. The method of claim 1, further comprising the steps of:
selecting a feature in the view of the data; and
entering at least one annotation that is to be associated with said selected feature of the data.

21. The method of claim 20, wherein said selection is accomplished via lassoing said feature with mouse movement.

22. The method of claim 20, wherein said selection is accomplished via mouse click.

23. The method of claim 20, wherein said entering of at least one annotation is accomplished via an object editor interface.

24. The method of claim 20, wherein said entering of at least one annotation is accomplished via free-form sketching.

25. The method of claim 20, wherein said entering of at least one annotation is accomplished via attachment of an external data file.

26. The method of claim 20, further comprising overlaying at least one of said entered annotations on said view of the data.

27. The method of claim 1, wherein said data comprises mass spectrometry data.

28. The method of claim 1, wherein said data comprises biological data.

29. The method of claim 1, wherein said data comprises chemical data.

30. The method of claim 1, further comprising selecting a portion of the data and automatically querying at least one database, based on the selection made.

31. The method of claim 30, wherein said database query triggers display of retrieved data in an associated viewer software.

32. The method of claim 31, wherein selection of a segment of said data in said associated viewer software triggers scrolling to display a set of features in said data that correspond to said segment of data in said associated viewer.

33. A method comprising forwarding a result obtained from the method of claim 1 to a remote location.

34. A method comprising transmitting data representing a result obtained from the method of claim 1 to a remote location.

35. A method comprising receiving a result obtained from a method of claim 1 from a remote location.

36. A system for displaying and manipulating data to facilitate identification, correlations or other useful relationships among the data, said system comprising:
means for generating a planar view of a 2-D projection of the data, which is continuously zoomable and scrollable,
means for reducing raw data to symbols representative of said raw data.

37. A system for comparing multiple data sets, comprising
means for fitting a scale and origin of one data set view set onto views of all other data sets of the multiple data sets, to provide windows on all of the data sets pointing to homologous locations,
means for color-coding said fitted data sets to visually distinguish said fitted data sets from each other; and
means for overlaying the color-coded, fitted, multiple data set views on a single window.

38. A computer readable medium carrying one or more sequences of instructions for displaying and manipulating data to facilitate identification, correlations or other useful relationships among the data, wherein execution of one or more sequences of instructions by one or more processors causes the one or more processors to perform the steps of:
generating a planar view of a 2-D projection of the data, which is continuously zoomable and scrollable.

* * * * *